US009757015B2

(12) United States Patent
Lei

(10) Patent No.: US 9,757,015 B2
(45) Date of Patent: Sep. 12, 2017

(54) IMAGING SYSTEMS AND METHODS FOR USING IN SPATIALLY CONSTRAINED LOCATIONS

(71) Applicant: OmniVision Technologies, Inc., Santa Clara, CA (US)

(72) Inventor: Junzhao Lei, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 318 days.

(21) Appl. No.: 14/260,010

(22) Filed: Apr. 23, 2014

(65) Prior Publication Data

US 2015/0312451 A1 Oct. 29, 2015

(51) Int. Cl.
*A61B 1/05* (2006.01)
*A61B 1/04* (2006.01)
*H04N 5/225* (2006.01)

(52) U.S. Cl.
CPC ............... *A61B 1/04* (2013.01); *A61B 1/05* (2013.01); *H04N 5/2253* (2013.01); *H04N 5/2258* (2013.01); *H04N 2005/2255* (2013.01)

(58) Field of Classification Search
CPC ............ H04N 5/2254; A61B 1/05; A61B 1/04
See application file for complete search history.

(56) References Cited

U.S. PATENT DOCUMENTS

| 2009/0128682 | A1* | 5/2009 | He | G03B 3/06 |
| | | | | 348/345 |
| 2011/0213204 | A1* | 9/2011 | Kuroda | A61B 1/05 |
| | | | | 600/109 |
| 2012/0307030 | A1* | 12/2012 | Blanquart | H01L 27/14601 |
| | | | | 348/76 |
| 2014/0111620 | A1* | 4/2014 | Park | H04N 13/0239 |
| | | | | 348/46 |
| 2015/0237991 | A1* | 8/2015 | Edgar | A45D 34/04 |
| | | | | 132/320 |

OTHER PUBLICATIONS

Simanek, "Mirror and Prism Methods for 3d Macro Photography," downloaded from http://www.lhup.edu/~dsimanek/3d/stereo/3dgallery16.htm, 2008.

(Continued)

*Primary Examiner* — Nam Pham
(74) *Attorney, Agent, or Firm* — Lathrop & Gage LLP

(57) ABSTRACT

An imaging system for use in a spatially constrained location includes an image sensor for capturing an image, wherein the image sensor has (a) a first rectangular area containing a pixel array and connecting circuitry communicatively coupled with the pixel array and (b) a second rectangular area with only one shared side with the first rectangular area and containing support electronics for pixel array control and signal acquisition, where the support electronics is communicatively coupled with the connecting circuitry. An imaging method for use in a spatially constrained location includes (a) forming an image of a scene on a pixel array of an image sensor contained within a first rectangular area having a first side and (b) communicating electrical signals between the pixel array and support electronics located onboard the image sensor and contained within a second rectangular area sharing only one side with the first rectangular area.

23 Claims, 15 Drawing Sheets

(56) References Cited

OTHER PUBLICATIONS

Keller, et al., "A Single-Imager Stereoscopic Endoscope," SPIE 7964, Medical Imaging 2011: Visualization, Image-Guided Procedures, and Modeling, 79641Z (Mar. 2, 2011); doi: 10.1117/12.873011.
Lindgren, "Topics on CMOS Image Sensor," Linkopings Universite, Institute of Technology, 2005.
Tabaee, et al., "Three-Dimensional Endoscopic Pituitary Surgery," Operative Neurosurgery 2, vol. 64, May 2009.
Translation of the First Office Action corresponding to Taiwanese Patent Application No. 104112723, dated Jul. 21, 2016, 4 pages.

* cited by examiner

IMAGING SYSTEMS AND METHODS FOR USING IN SPATIALLY CONSTRAINED LOCATIONS

BACKGROUND

The demand for compact camera systems delivering high performance is increasing with the growing use of imaging systems in a wide variety of applications. Such applications are found in areas such as consumer electronics, machine vision, automotive, and medical diagnostics and procedures.

Medical endoscopes used to examine an interior part of the human body constitute an example with challenging requirements to the size of the camera system. The camera system, including at least an image sensor, optics, and electronics, must fit within the area to be examined. Preferably, the camera system is sufficiently compact that there is room for navigating the camera to inspect the environment in a desired direction. Additionally, the camera system is often guided to the area of interest via passageways, such as an artery, which in itself imposes size constraints. Concurrently, the imaging capability and performance of a medical endoscope camera system is essential for reaching the desired outcome of the procedure, for instance an accurate diagnosis or a successful operation. For example, many procedures will benefit from high-resolution imaging to obtain sufficiently detailed information. However, the spatial requirements imposed by the use scenario limits the achievable performance of medical endoscope camera systems. Likewise, the size of endoscope cameras limits the use of medical endoscopes.

SUMMARY

In an embodiment, an imaging system for use in a spatially constrained location includes an image sensor for capturing an image, wherein the image sensor has (a) a first rectangular area containing a pixel array and connecting circuitry communicatively coupled with the pixel array and (b) a second rectangular area with only one shared side with the first rectangular area and containing support electronics for pixel array control and signal acquisition, where the support electronics is communicatively coupled with the connecting circuitry.

In an embodiment, an imaging method for use in a spatially constrained location includes (a) forming an image of a scene on a pixel array of an image sensor contained within a first rectangular area having a first side and (b) communicating electrical signals between the pixel array and support electronics located onboard the image sensor and contained within a second rectangular area sharing only one side with the first rectangular area.

DETAILED DESCRIPTION OF THE EMBODIMENTS

Figure 1:
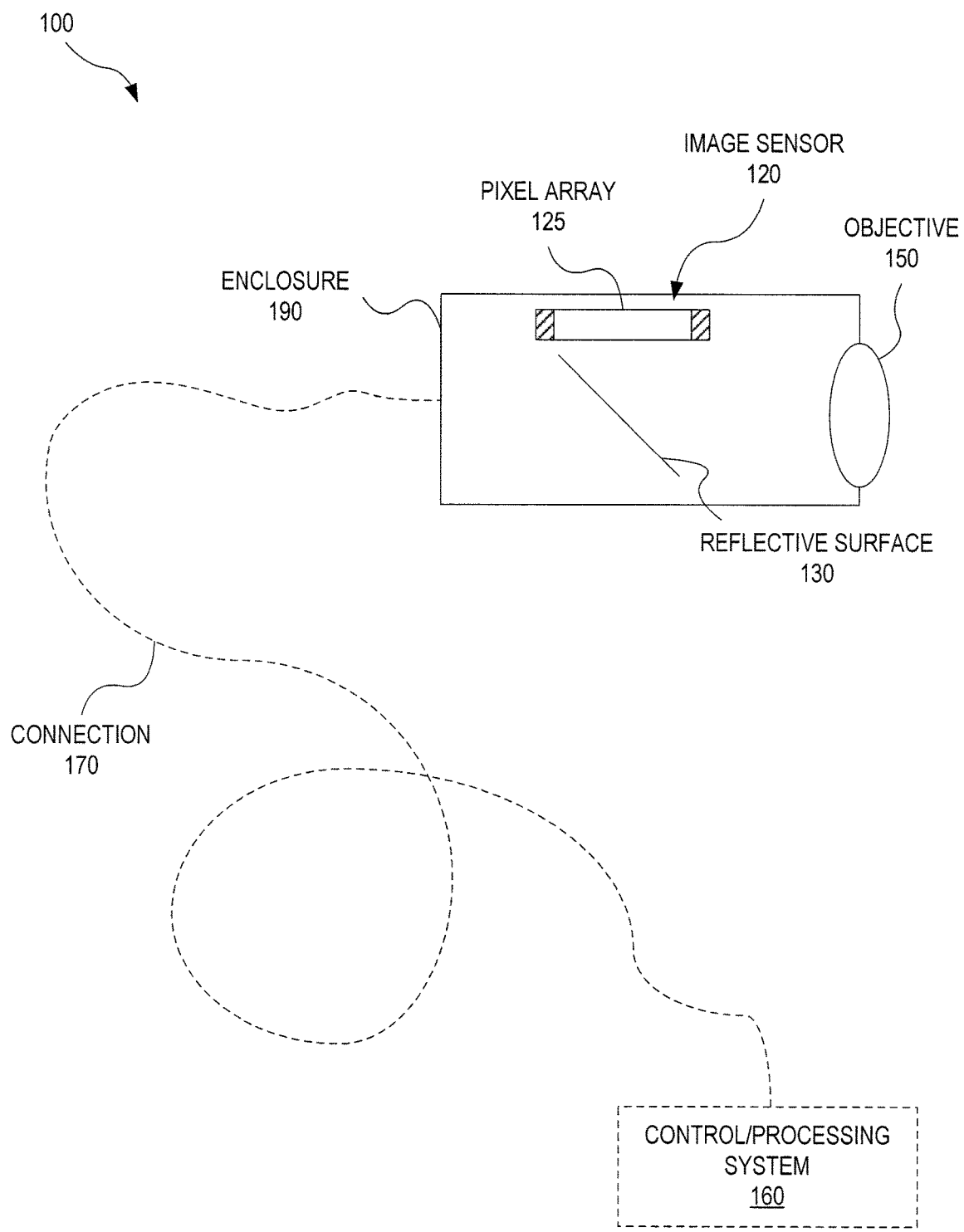
FIG. 1 illustrates an imaging system for use in a spatially constrained location, according to an embodiment.

Disclosed herein are imaging systems and methods for use in spatially constrained locations. The presently disclosed imaging systems and methods have utility in a range of applications. For example, endoscopic camera systems, especially those associated with medical procedures, often impose strict spatial requirements. Other applications include consumer electronics, where the demand for smaller devices with greater performance persists.

Disclosed herein are image sensors having an asymmetric configuration. These image sensors include a photosensitive pixel array for capturing an image formed thereupon, support electronics, and connectors connecting the pixel array to the support electronics. The pixel array generates, for each pixel thereof, an electrical signal corresponding to the amount of light incident thereupon. The support electronics may include functionality such as readout control, gain control, timing control, and/or amplification, to generate an electrical image signal representative of the image formed upon the pixel array. Unlike conventional image sensors, where a rectangular pixel array is surrounded by support electronics on all four sides of the rectangle, the support electronics of the asymmetric image sensors disclosed herein is located to one side of the pixel array. Consequently, one side length of the present asymmetric image sensors may be larger than a conventional image sensor having the same size pixel array. However, the orthogonal side length may be made significantly smaller than that of conventional image sensors. When implemented in the presently disclosed imaging systems having a folded imaging path, the necessary camera elements may be packed in a smaller enclosure than that of conventional systems.

Also disclosed herein are imaging systems with a folded imaging path. These systems include a reflective surface for redirecting light transmitted by an imaging objective towards a pixel array for imaging. In an embodiment, the pixel array is oriented such that its surface normal is substantially orthogonal to the optical axis of the imaging objective. In certain embodiments, the asymmetric image sensors discussed above are advantageously implemented in the imaging systems having a folded imaging path. This combination offers particular benefits as the asymmetric image sensor may be positioned to utilize the available space more efficiently than a conventional image sensor.

In certain embodiments, the imaging systems disclosed herein further include a second image sensor located to capture an image of light transmitted by the reflective surface. This image sensor may have different properties than the image sensor capturing an image of the reflected light, for example different resolution or different sensitivity. Alternatively, or in combination therewith, one of the two image sensors may be a monochrome image sensor while the other may be a color-sensitive image sensor. These embodiments may provide more functionality than what is achievable with a single-camera system, while complying with tight spatial constraints.

FIG. 1 illustrates one exemplary imaging system 100 for use in a spatially constrained location. Imaging system 100 includes an image sensor 120, an imaging objective 150, a reflective surface 130, and an enclosure 190. Image sensor 120 further includes a pixel array 125. Image sensor 120, imaging objective 150, and reflective surface 130 are configured such that imaging objective 150 forms an image of a scene on pixel array 125. Optionally, imaging system 100 further includes a control/processing system 160 for processing of images captured by image sensor 120 and/or control of image capture by image sensor 120 as well as other functionality of components within enclosure 190. Optional control/processing system 160 communicates with image sensor through an optional connection 170. Imaging system 100 is, for example, a medical endoscope system. Enclosure 190 provided structural support and/or environmental protection for image sensor 120, reflective surface 130, and imaging objective 150. Enclosure 190 may only partly enclose imaging objective 150, as illustrated in FIG. 1, or enclosure 190 may fully enclose imaging objective 150 while allowing light from a scene to reach imaging objective 150.

In an embodiment, pixel array 125 and imaging objective 150 are configured such that the optical axis of imaging objective 150 is substantially orthogonal to a surface normal of pixel array 125. In the present disclosure, the term "substantially orthogonal" is to be interpreted as deviating from orthogonal by no more than 10 degrees. Certain embodiments may benefit from the optical axis of imaging objective 150 being exactly orthogonal to a surface normal of pixel array 125. However, as known by a person skilled in the art, manufacturing tolerances and other non-idealities such as drift over time may preclude exact orthogonality. Further, some embodiments may be relatively insensitive to the exact angle between the optical axis of imaging objective 150 and a surface normal of pixel array 125 as long as it is near orthogonal. For such embodiments, strict tolerances to the angle between the optical axis of imaging objective 150 and a surface normal of pixel array 125 may impose unnecessary requirements on both the design and manufacture of imaging system 100. Under most circumstances, it is possible to manufacture imaging system 100 such that an angle between the optical axis of imaging objective 150 and a surface normal of pixel array 125 within the range from 80 to 100 degrees is maintained. Likewise, following similar arguments, the term "substantially parallel" is in the present disclosure to be interpreted as deviating from parallel by no more than 10 degrees.

Image sensor 120 is, for example, a complementary metal-oxide-semiconductor (CMOS) image sensor or a charge-coupled device (CCD) image sensor. In an embodiment, image sensor 120 is a CMOS image sensor providing an analog output. In one embodiment, reflective surface 130 is fully reflective. In another embodiment, reflective surface is partially reflective. In the latter embodiment, imaging system 100 includes a second image sensor (not shown in FIG. 1) for capture of an image based upon light propagating from imaging objective 150 and transmitted by reflective surface 130. In an embodiment, enclosure 190 is cylindrical, with the axis of the cylinder being approximately parallel to the optical axis of the imaging objective. While FIG. 1 illustrates imaging objective 150 as being a single lens, imaging objective 150 may include multiple lenses, as well as one or more other elements such as a filter or an aperture.

Figure 2:
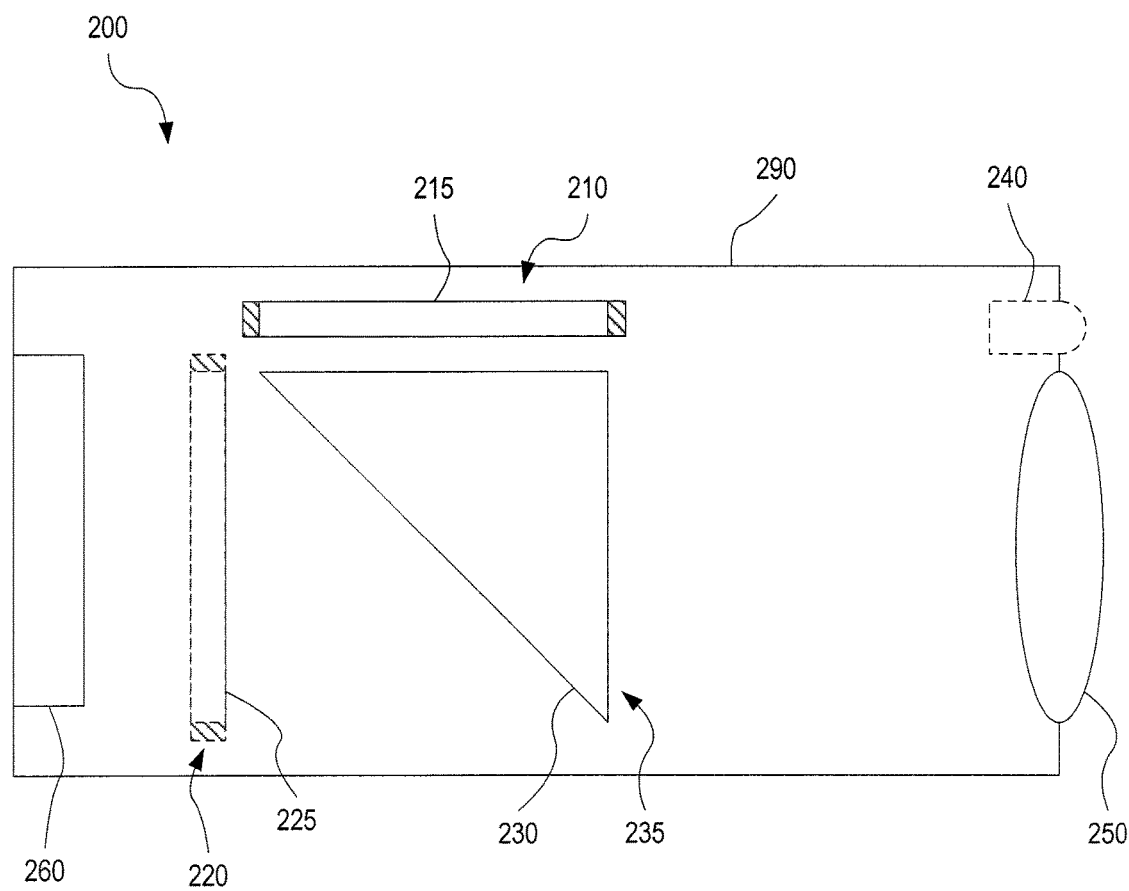
FIG. 2 illustrates an embodiment of the system of FIG. 1, wherein an imaging path is folded by using a prism, according to an embodiment.

FIG. 2 illustrates one exemplary imaging system 200 for use in a spatially constrained location. Imaging system 200 is an embodiment of imaging system 100 of FIG. 1. Imaging system 200 includes an image sensor 210, an imaging objective 250, a prism 235, an interface 260, and an enclosure 290. Image sensor 210 is an embodiment of image sensor 120 (FIG. 1) and includes a pixel array 215, which is an embodiment of pixel array 125. Imaging objective 250 is an embodiment of imaging objective 150 (FIG. 1). Enclosure 290 is an embodiment of enclosure 190 (FIG. 1). Prism 235 includes a surface 230, which is an embodiment of reflective surface 130 (FIG. 1). In one embodiment, surface 230 reflects at least a portion of light transmitted by imaging objective 250 by internal reflection due to the difference in refractive index between prism 235 and the surrounding medium. For example, prism 235 is made of glass or plastic with a refractive index in the range from 1.45 to 1.75, while the surrounding medium is air with a refractive index of 1.0. In another embodiment, surface 230 includes a coating to achieve a desired reflection coefficient such as greater than 90%, greater than 95%, or between 45 and 55%. The coating is, for example, a dielectric coating or a metal coating.

Optionally, imaging system 200 includes a second image sensor 220 having a pixel array 225. Optional image sensor 220 captures an image from light transmitted by surface 230. The properties, both form factor and imaging properties, of image sensor 220 may be different from those of image sensor 210. For example, image sensor 210 and optional image sensor 220 have different resolution or different sensitivity. Alternatively, or in combination therewith, one of image sensor 210 and optional image sensor 220 may be a monochrome image sensor while the other may be a color-sensitive image sensor.

Imaging objective 250 and image sensor 210 are configured such that the optical axis of imaging objective 250 is substantially perpendicular to a surface normal of pixel array 215. Optional image sensor 220 is positioned such that a surface normal to pixel array 225 is substantially parallel to the optical axis of imaging objective 250. In certain embodiments, reflective surface 230 is configured such that a surface normal thereto is at a substantially 45 degree angle with the optical axis of imaging objective 250 and with a surface normal of pixel array 215.

In certain embodiments, imaging system 200 further includes a light source 240 for illuminating a scene. Light source 240 has utility, for example, in medical endoscopy and other use scenarios where the area to be imaged is either dark or under-illuminated.

Although not shown in FIG. 2, an alternate embodiment of imaging system 200 includes control/processing system 160 and connection 170.

Figure 3:
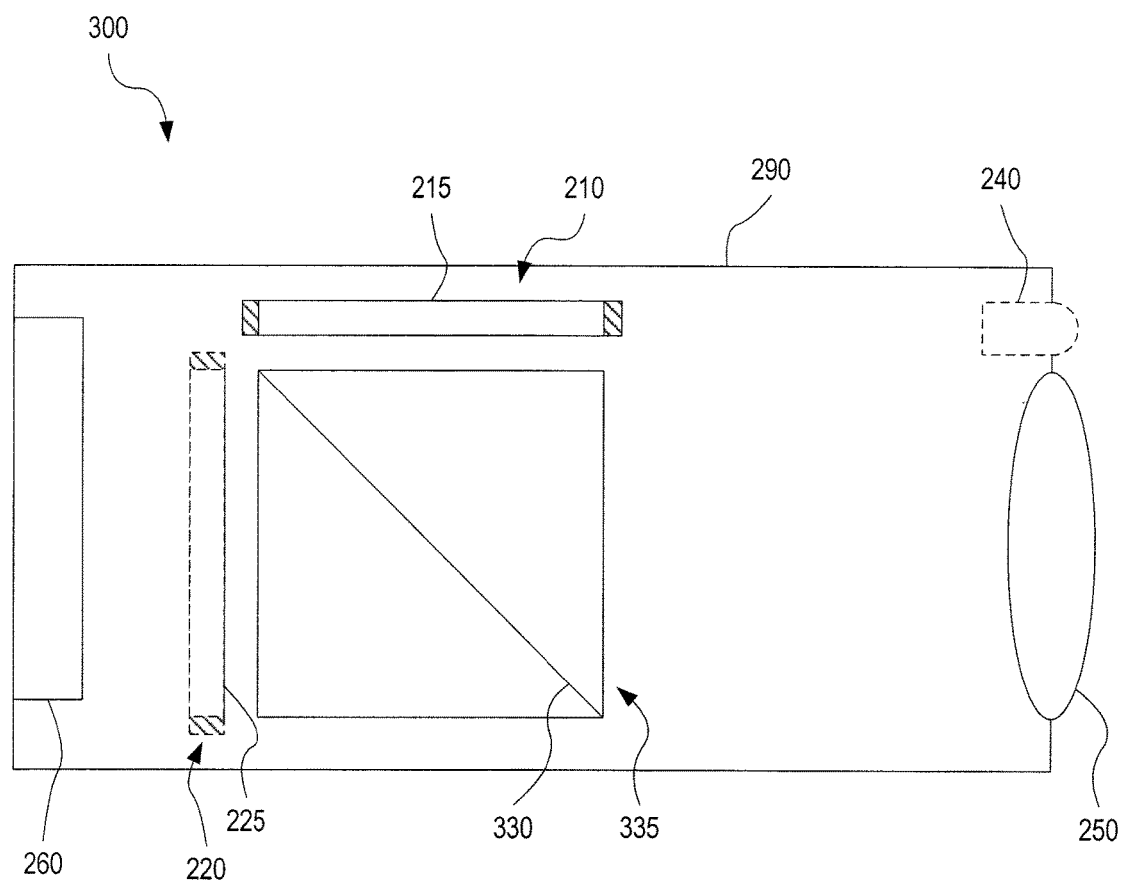
FIG. 3 illustrates an embodiment of the system of FIG. 1, wherein an imaging path is folded by using a beam splitter cube, according to an embodiment.

FIG. 3 illustrates one exemplary imaging system 300 for use in a spatially constrained location. Imaging system 300 is an embodiment of imaging system 100 of FIG. 1. Imaging system 300 is similar to imaging system 200 of FIG. 2, except that beam splitter cube 335 replaces prism 235 of imaging system 200. Beam splitter cube 335 includes an interface 330, which is an embodiment of reflective surface 130 (FIG. 1).

Figure 4:
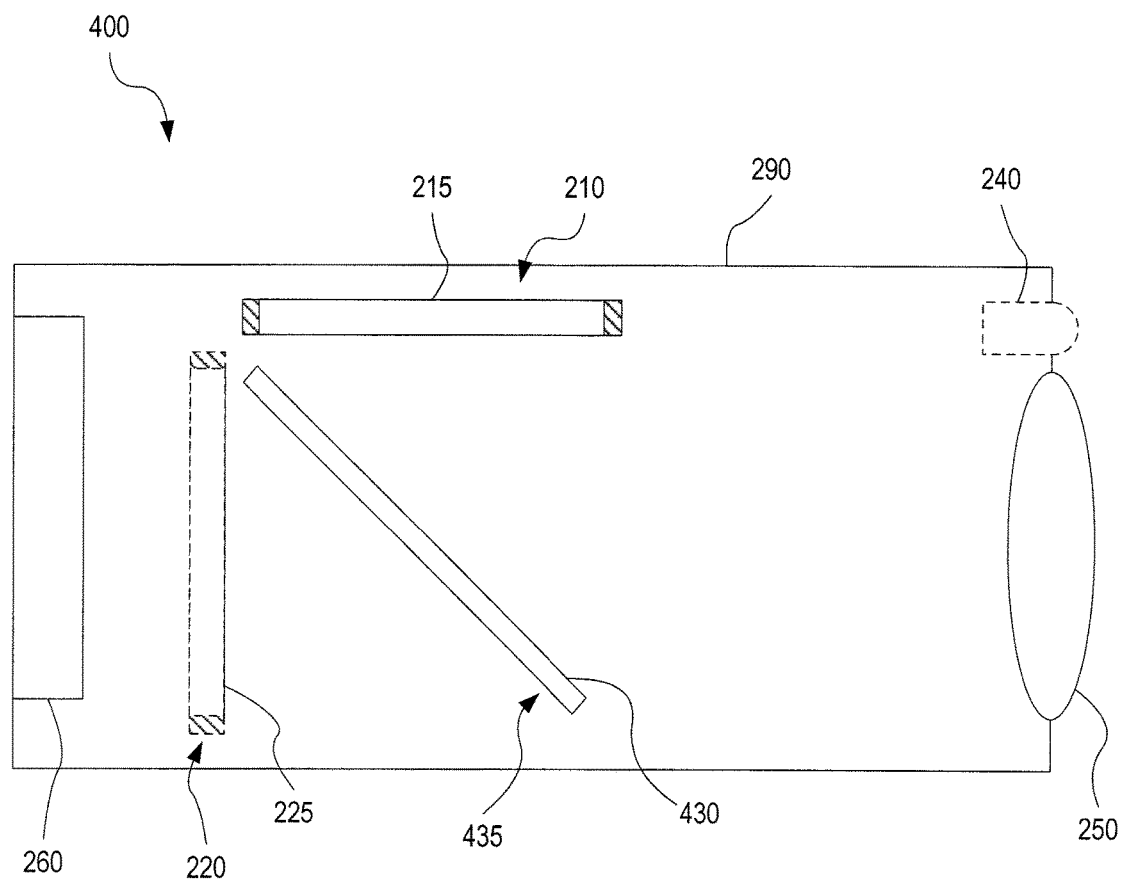
FIG. 4 illustrates an embodiment of the system of FIG. 1, wherein an imaging path is folded by using a mirror, according to an embodiment.

FIG. 4 illustrates one exemplary imaging system 400 for use in a spatially constrained location. Imaging system 400 is an embodiment of imaging system 100 of FIG. 1. Imaging system 400 is similar to imaging system 200 of FIG. 2, except that a mirror 435 replaces prism 235 of imaging system 200. Mirror 435 includes a surface 430, which is an embodiment of reflective surface 130 (FIG. 1). Surface 430 may be on the side of mirror 435 that faces imaging objective 250, as illustrated in FIG. 4, or on the side of mirror 435 that faces away from imaging objective 250. Surface 430 may include a dielectric coating or a metal coating for producing the desired reflective properties, as discussed in connection with imaging system 200 of FIG. 2.

Figure 5:
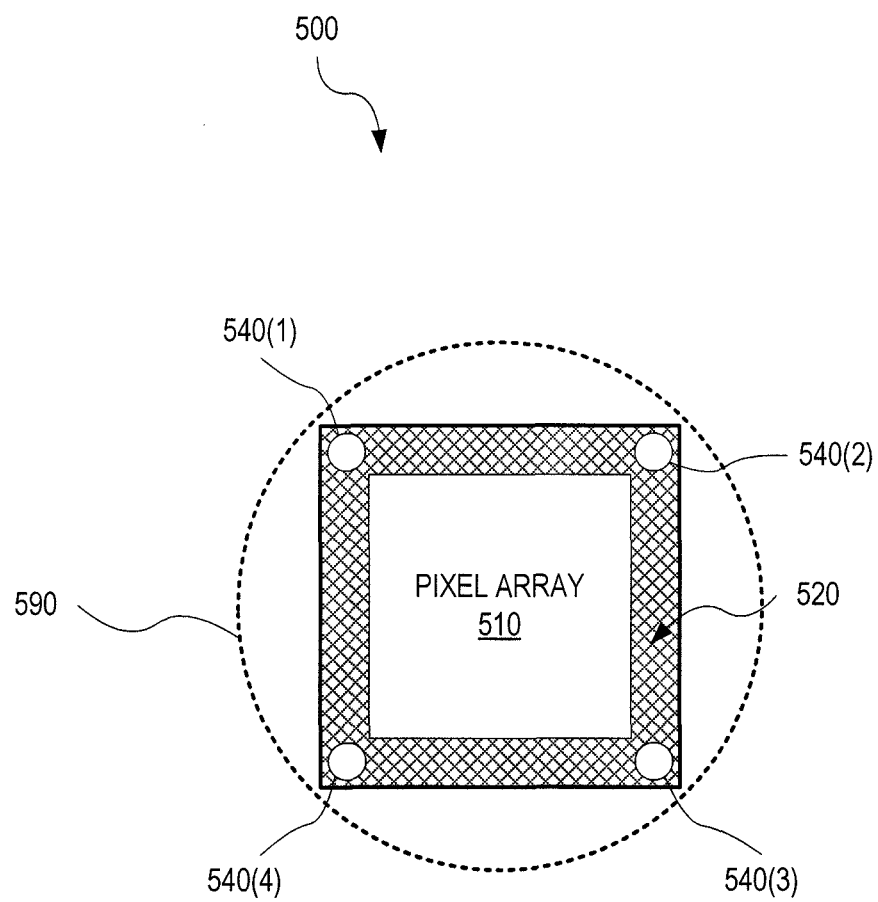
FIG. 5 illustrates a prior art image sensor.

FIG. 5 illustrates a prior art image sensor 500. Prior art image sensor 500 includes a pixel array 510, electronic circuitry 520, and solderable connectors 540. Electronic circuitry 520 includes support electronics for the operation of pixel array 510. Connectors 540 are objects, such as pins, for establishing connections between prior art image sensor 500 and a system external thereto. When implemented in a conventional medical endoscope camera having a cylindrically shaped enclosure, prior art imaging system 500 is oriented such that a surface normal to pixel array 510 is parallel to the axis of the cylinder. Bounding circle 590 illustrates the minimal circumference that the cylinder must have to fit within it prior art image sensor 500.

Figure 6:
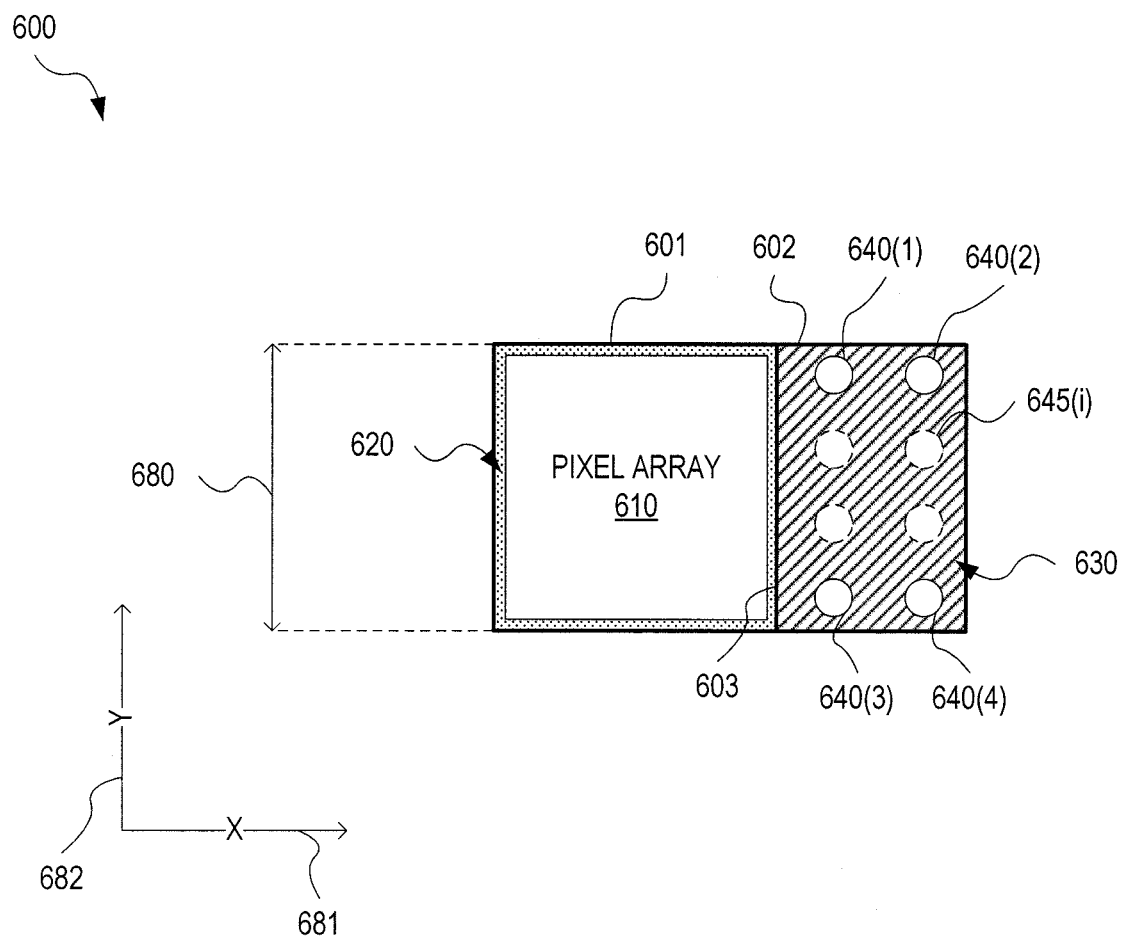
FIG. 6 illustrates an asymmetric image sensor, for use in a spatially constrained location, with support electronics being located to one side of the pixel array, according to an embodiment.

FIG. 6 illustrates, in top-plan view, one exemplary image sensor 600 for use in a spatially constrained location. Image sensor 600 is advantageously implemented as image sensor 120 of FIG. 1, or as image sensor 210 of FIGS. 2, 3, and 4. Image sensor 600 includes a pixel array 610, support electronics 630, and connecting circuitry 620 for connecting pixel array 610 and support electronics 630. Pixel array 610 generates an electrical response to light incident thereupon. Support electronics 630 includes functionality associated with conditioning of pixel array 610 to produce the electrical response. Support electronics 630 further includes functionality for processing electrical signals generated by pixel array 610, in response to incident light, to produce an electrical image signal representative of the image found on pixel array 610. Support electronics 630 may include functionality such as readout control, gain control, timing control, and/or amplification, to generate the electrical image signal. Connecting circuitry 620 includes connectors for connecting pixels of pixel array 610 with support electronics 630. In certain embodiments, connecting circuitry includes connections only.

Support electronics 630 is located proximate one side of pixel array 610, while the other three sides of pixel array 610 are associated with connecting circuitry only. Pixel array 610 and connecting circuitry 620 are contained within a first rectangular area 601. Support electronics 630 is contained within a second rectangular area 602, which shares only one side 603 with the first rectangular area. Support electronics 630 includes four connectors 640 for establishing connections between support electronics 630 and a system external thereto, such as interface 260 of FIGS. 2, 3, and 4. Optionally, support electronics 630 includes additional optional connectors 645.

In an embodiment, the extent of support electronics 630, in the dimension parallel to shared side 603, is no greater than the extent of pixel array 610 and connecting circuitry 620 in that same dimension. Referring to the coordinate system consisting of x-axis 681 and y-axis 682, the dimension considered here is the y-dimension. The extent of pixel array 610 and connecting circuitry 620 in this dimension is indicated by arrow 680. In another embodiment, the extent of support electronics 630, in the dimension parallel to the shared side 603, is similar to the extent of pixel array 610 and connecting circuitry 620 in that same dimension. In yet another embodiment, the length of the side of pixel array 610, closest to shared side 603, is at least 90% of the extent of support electronics 630 in the dimension parallel to that same side. The extent of support electronics 630 in the direction away from pixel array 610 may be increased or decreased as compared to the illustration in FIG. 6, without departing from the scope hereof. In certain embodiments, image sensor 600 is formed of a single die, such that pixel array 610, connecting circuitry 620, and support electronics 630 are on the same die. This facilitates short connections in connecting circuitry 620 between pixel array 610 and support electronics 630. Hence, this embodiment may provide improved performance over systems where pixel array 610 and support electronics 630 are on separate dies. In an embodiment, image sensor 600 is implemented in an endoscope, for example a medical endoscope.

The configuration of image sensor 600 facilitates implementation into systems that impose tight spatial constraints on the extent of the image sensor in one dimension within the plane of the pixel array, while having more relaxed or no spatial constraints in the dimension orthogonal thereto within the plane of the pixel array. Image sensor 600 may be oriented such that shared side 603 is in the dimension associated with tighter spatial constraints. In one embodiment, all sides of rectangular area 601 are less than 1 millimeter in length. In another embodiment, all sides of rectangular area 601 are less than 2 millimeters in length.

In an embodiment, pixel array 610 has dimensions identical to the dimensions of pixel array 510 of prior art image sensor 500 (FIG. 5). However, all support electronics of image sensor 630 is located within rectangular area 602, proximate only one side of pixel array 610. Therefore, the extent of image sensor 600 in the dimension parallel to shared side 603 may be made smaller than the corresponding extent of prior art image sensor 500, where support electronics surrounds pixel array 510 on all four sides.

In an embodiment, support electronics 630 is configured such that a first, second, and third one of connectors 640 receives power, electrical ground connection, and a clock signal, respectively, from an external source, while a forth one of connectors 640 communicates an output signal to an external system. The output signal is, for example, an electrical image signal representative of the image captured by image sensor 600. As compared to prior art image sensor 500 of FIG. 5, image sensor 600 further includes additional optional connectors 645. While prior art image sensor 500 only has room for four connectors 540 (FIG. 5), support electronics 630 of image sensor 600 may accommodate any number of optional connectors 645 in addition to the four connectors 640 by appropriately sizing the area of support electronics 630. Conventional image sensors, such as prior art image sensor 500, require four connections for receiving power, electrical ground, and a clock signal, as well as outputting an image signal. Support electronics 630 may utilize optional connectors for receiving additional signals, for example to control one or more of exposure time, gain, and white balance. Support electronics 630 may further utilize the additional pins for receiving a negative voltage required to operate pixel arrays with very small pixels. An increase in the extent of support electronics 630 in the direction away from pixel array 610 would allow for a larger number of optional connectors 645 than the four shown in FIG. 6. Such an increase is not associated with an increased extent of support electronics 630 in the dimension parallel to the shared side. In certain embodiments, connectors 640 and optional connectors 645 are solderable connectors. In addition to accommodating additional connectors 645, as compared to prior art image sensor 500, support electronics 630 may accommodate additional functionality such as analog-to-digital conversion. Furthermore, the additional connectors 645 may facilitate functionality within support electronics 630 such as automatic gain control and/or automatic white balance. Such functionality may serve to provide the desired image quality under varying conditions.

Figure 7A:
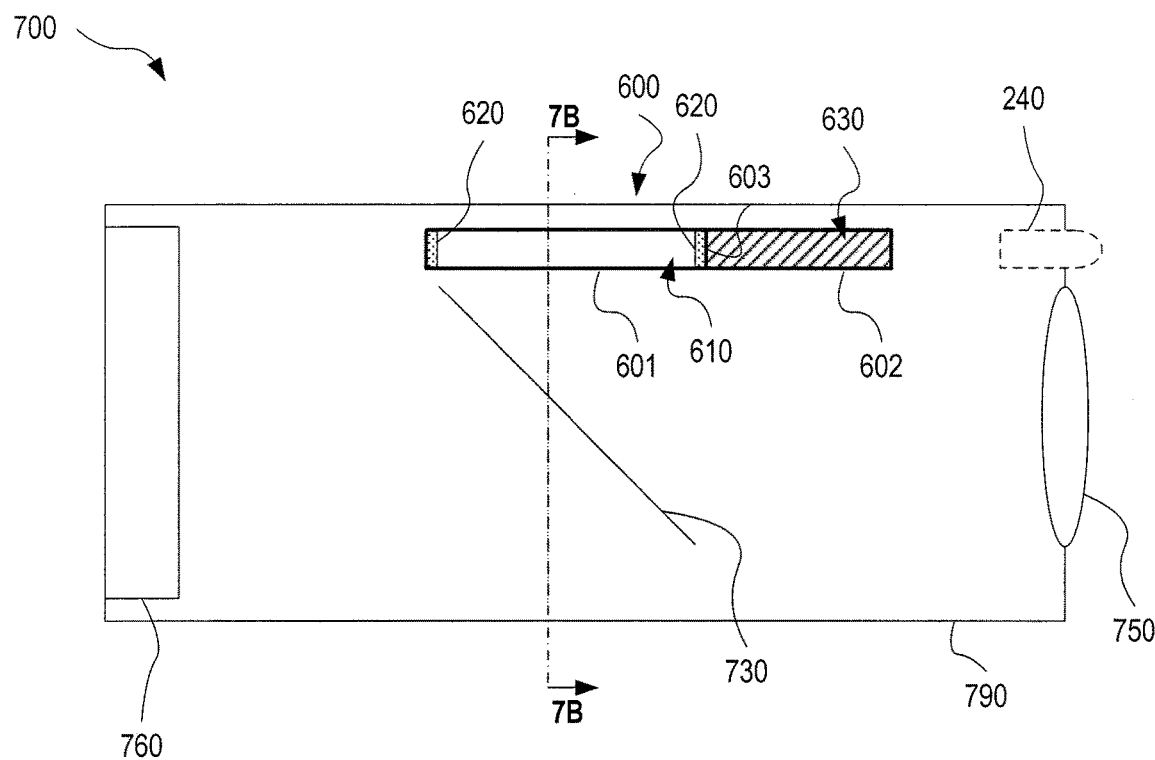
FIG. 7A illustrates, in a cross-sectional view, an embodiment of the system of FIG. 1 implemented with the image sensor of FIG. 6, according to an embodiment.
Figure 7B:
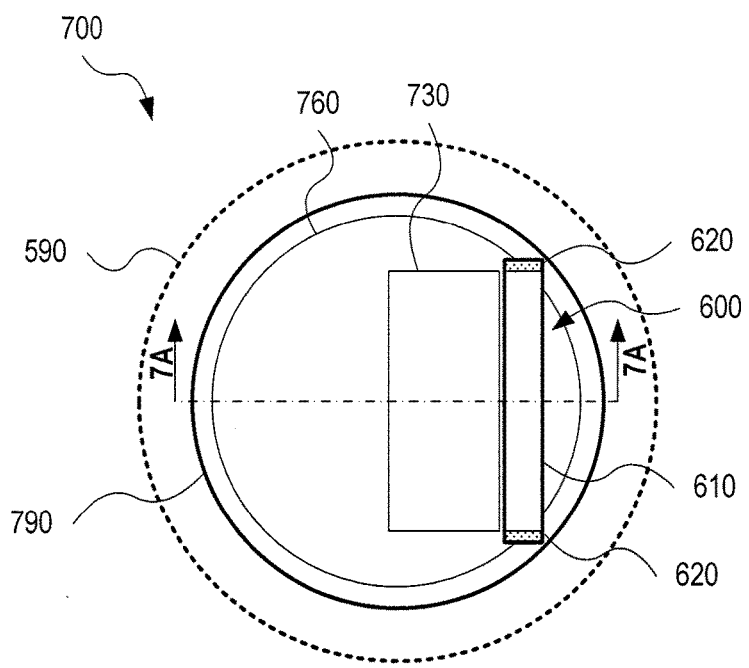
FIG. 7B illustrates the imaging system of FIG. 7A in a cross sectional view orthogonal to the cross sectional view used in of FIG. 7A.

FIGS. 7A and 7B illustrate, in mutually orthogonal cross-sectional views, one exemplary imaging system 700 for use in a spatially constrained location. FIGS. 7A and 7B are sometimes collectively referred to herein as FIG. 7. Imaging system 700 utilizes image sensor 600 of FIG. 6. Imaging system 700 is an embodiment of imaging systems 100 of FIG. 1, 200 of FIG. 2, 300 of FIG. 3, and 400 of FIG. 4, with image sensor 600 (FIG. 6) implemented as image sensor 210 (FIGS. 2, 3, and 4). In certain embodiments, imaging system 700 is implemented in an endoscope. Imaging system 700 includes image sensor 600 (FIG. 6), a reflective surface 730, an imaging objective 750, an interface 760, an enclosure 790, and, optionally, light source 240 (FIGS. 2, 3, and 4). Imaging objective 750 is an embodiment of imaging objective 250 (FIGS. 2, 3, and 4). Reflective surface 730 may be implemented using a prism, as illustrated in FIG. 2, a beam splitter cube, as illustrated in FIG. 3, a mirror, as illustrated in FIG. 4, or as any other surface or interface capable of reflecting light, without departing from the scope hereof. Enclosure 790 is an embodiment of enclosure 290 (FIGS. 2, 3, and 4), and is cylindrical in shape. Enclosure 790 may have other shapes without departing from the scope hereof. For example, enclosure 790 may have a substantially oval cross section, be a rectangular cuboid, or be a rectangular cuboid with rounded edges. Although not shown in FIG. 7, an alternate embodiment of imaging system 700 includes control/processing system 160 and connection 170.

FIG. 7A shows imaging system 700 in a cross-sectional view, where the cross section is taken in the plane spanned by the optical axis of imaging objective 750 and a surface normal to pixel array 610. Image sensor 600 is configured such that support electronics 630 (FIG. 3) extends away from pixel array 610 in a direction along the optical axis of imaging objective 750. The optical axis of imaging objective 750 is substantially parallel to the cylinder axis of enclosure 790. FIG. 7B shows imaging system 700 in a cross-sectional view, where the cross section is taken in the plane orthogonal to the optical axis of imaging objective 750 and parallel to a surface normal of pixel array 610, along line 7B-7B of FIG. 7A. The extent of image sensor 600 downwards limits the diameter of enclosure 790 in the dimension parallel to the side of pixel array 610 (FIG. 6) proximate support electronics 620. The extent of image sensor 600 in this dimension is defined by the extent of pixel array 610 and connecting circuitry 620 (FIG. 6). For comparison, assuming that pixel array 610 has the same area as pixel array 510 of image sensor 500 (FIG. 5), bounding circle 590 (FIG. 5) is illustrated in FIG. 7B. It is evident that the diameter of enclosure 790 is significantly smaller than that of bounding circle 590. Hence, the asymmetric configuration of image sensor 600 is capable of providing a more compact camera solution.

In an embodiment, system 700 is a medical endoscope camera. The associated use environment imposes tight spatial constraints on the camera in the dimensions orthogonal to the optical axis of the imaging objective and more relaxed spatial constraints in the dimension parallel to the optical axis of the imaging objective. A common requirement to medical endoscope cameras is that the camera, for example imaging system 700 without optional control/processing system 160 and optional connection 170, may have extent no greater than 10 millimeters in the dimensions orthogonal to the optical axis of the imaging objective.

While FIGS. 7A and 7B illustrate image sensor 600 configured such that support electronics 630 is closer than pixel array 610 to imaging objective 750, image sensor 600 may be reconfigured such that support electronics 630 is farther away from imaging objective 750, without departing from the scope hereof. For example, image sensor 600 may have a configuration within imaging system 700, which corresponds to a rotation of image sensor 600, as illustrated in FIG. 7A, by 180 degrees about a surface normal of pixel array 610, without departing from the scope hereof.

In an embodiment, image sensor 600 is positioned as close as possible to reflective surface 730. For example, the distance between pixel array 610 and the object providing reflective surface 730 may be defined by the thickness of a cover glass (not shown in FIGS. 6 and 7) over pixel array 610. In another embodiment, the distance between imaging objective 750 and the object providing reflective surface 730 is less than 3 millimeters.

Figure 8:
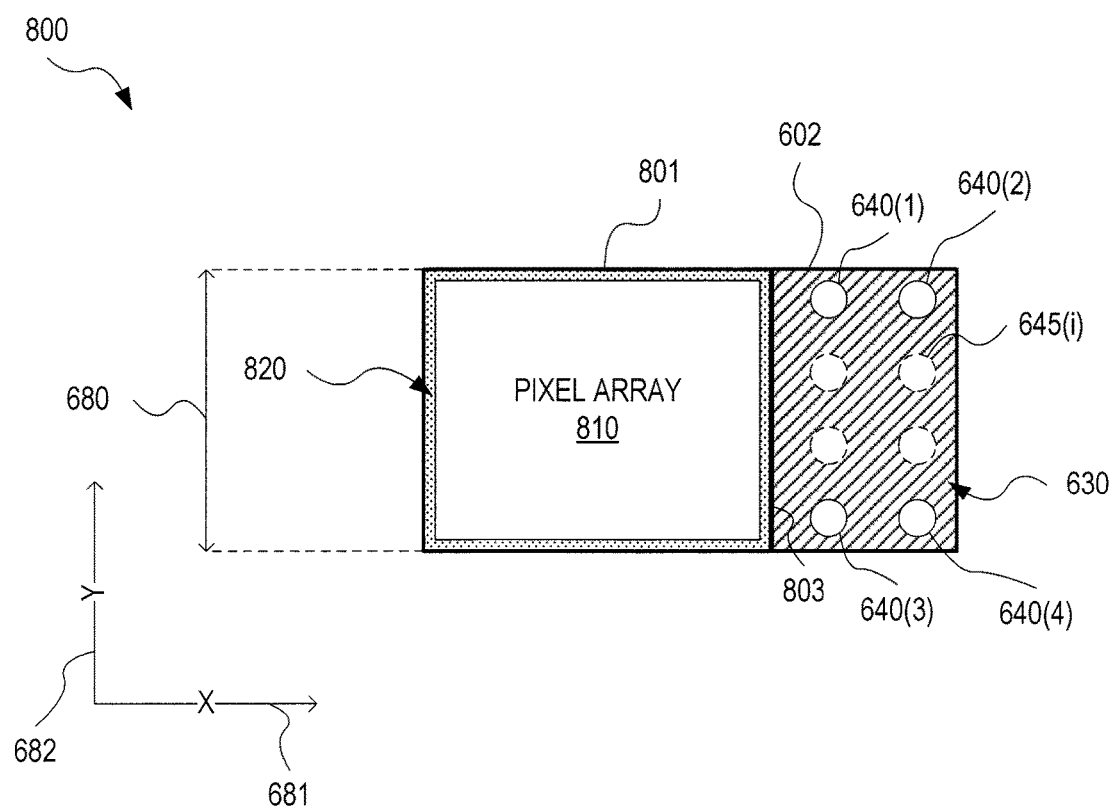
FIG. 8 illustrates an embodiment of the system of FIG. 1 implemented with the image sensor of FIG. 6, according to an embodiment.

FIG. 8 illustrates, in top-plan view, one exemplary image sensor 800 for use in a spatially constrained location. Image sensor 800 is a modification of image sensor 600 of FIG. 6. Image sensor 800 is advantageously implemented as image sensor 120 of FIG. 1, or as image sensor 210 of FIGS. 2, 3, and 4. Image sensor 800 may further be implemented in system 700 of FIG. 7 in place of image sensor 600. Image sensor 800 includes a rectangular pixel array 810, support electronics 630 (FIG. 6), and connecting circuitry 820 for connecting pixel array 810 to support electronics 630. Rectangular pixel array 810 and connecting circuitry 820 are contained within a rectangular area 801. Support electronics 630 is contained within rectangular area 602 (FIG. 6). Rectangular areas 801 and 602 share only one side 803. Rectangular pixel array 810 has mutually orthogonal shorter and longer sides, where the shorter side is substantially parallel to shared side 803.

As compared to pixel array 610 (FIG. 6) of image sensor 600, pixel array 810 and connecting circuitry 820 are extended in the direction away from support electronics 630.

Referring to the coordinate system defined by x-axis 681 (FIG. 6) and y-axis 682 (FIG. 6), pixel array 810 and connecting circuitry 820 are extended in the x-dimension. The extent of pixel array 810 and connecting circuitry 820 is unchanged in the y-dimension, as compared to image sensor 600, and equals extent 680 (FIG. 6). When implemented in system 700, in place of image sensor 600, image sensor 800 is extended in the direction substantially along the optical axis of imaging objective 750 (FIG. 7). In the medical endoscope camera embodiment of system 700, discussed in connection with FIG. 7, image sensor 800 is extended in the less restricted dimension of system 700. Image sensor 800 thus provides images of a different aspect ratio than those of image sensor 600, without conflicting with spatial constraints and without size reduction of pixel array 810 in any dimensions as compared to pixel array 610.

Figure 9:
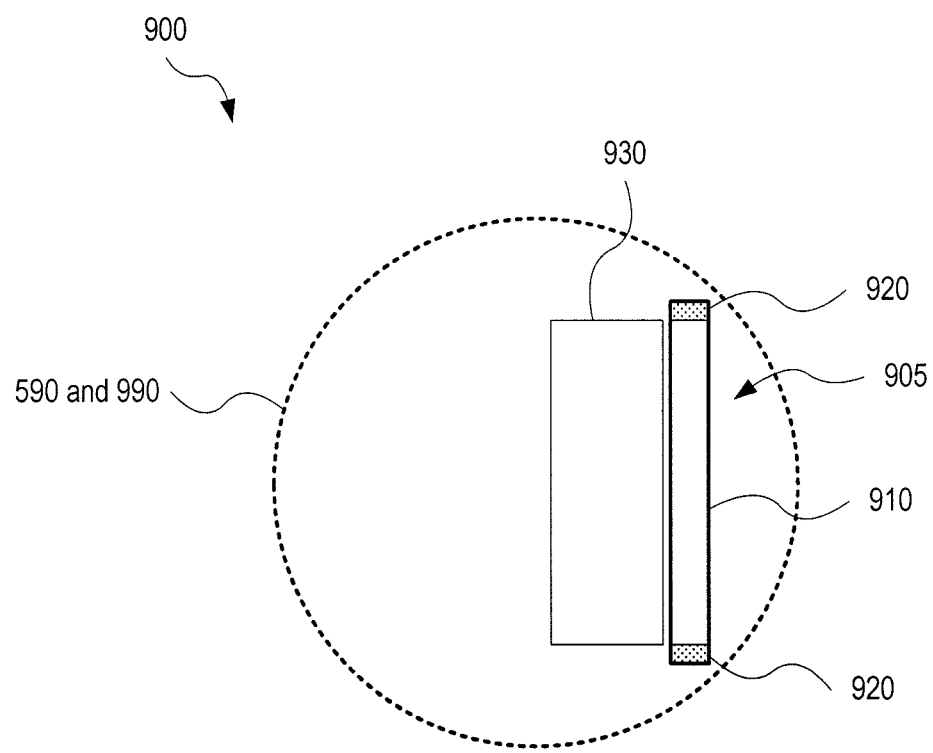
FIG. 9 illustrates an embodiment of the imaging system of FIG. 7 implemented with an enlarged embodiment of the image sensor of FIG. 6, according to an embodiment.

FIG. 9 illustrates, in cross-sectional view, one exemplary imaging system 900 for use in for use in a spatially constrained location. Imaging system 900 is a modification of imaging system 700 (FIG. 7). An image sensor 905 replaces image sensor 600 (FIGS. 6 and 7), a reflective surface 930 replaces reflective surface 730 (FIG. 7), and a cylindrical enclosure 990 with a diameter equal to the diameter of bounding circle 590 (FIG. 5) replaces enclosure 790 (FIG. 7). Image sensor 905 is a scaled up version of image sensor 600 (FIGS. 6 and 7). Image sensor 905 includes a pixel array 910, connecting circuitry 920, and support electronics (not shown in FIG. 9). The support electronics of image sensor 905 is disposed relative to pixel array 910 and connecting circuitry as is the case for support electronics 630 (FIGS. 6 and 7) relative to pixel array 610 (FIGS. 6 and 7) and connecting circuitry 620 (FIGS. 6 and 7).

As in the case of imaging system 700 in FIG. 7B, FIG. 9 illustrates imaging system 900 in a cross sectional view, where the cross section is taken in the plane orthogonal to the optical axis of imaging objective 750 and parallel to a surface normal of, pixel array 910, along line 7B-7B of FIG. 7A. Image sensor 910 is a modification of image sensor 600 (FIG. 6) scaled up in size to fit within bounding circle 590, and utilize the space therewithin. Reflective surface 930 is a correspondingly scaled up version of reflective surface 730.

In an example, pixel array 510 of prior art image sensor 500 (FIG. 5) has 280×280 pixels and occupies 52% of the surface area of the light receiving face of prior art image sensor 500. In comparison, by utilizing the image sensor configuration discussed in connection with FIG. 6 and the imaging system configuration discussed in connection with FIG. 7, pixel array 910 of image sensor 905 may have 360×360 pixels, where each such pixel has the same size as a pixel of pixel array 510. Further, pixel array 910 occupies 86% of the area occupied by pixel array 910 and connecting circuitry 920. This example demonstrates that the image sensor configuration discussed in connection with FIG. 6, in combination with the imaging system configuration discussed in connection with FIG. 7, provides increased pixel resolution with an increase in the number of pixels by 65%, as compared to prior art image sensor 500. In an alternate example, pixel array 910 has the same number of pixels as pixel array 510, but the area of each pixel is increased by 33%, as compared to pixel array 510. This solution provides increased photosensitivity of image sensor 905 as compared to prior art image sensor 500.

Figure 10A:
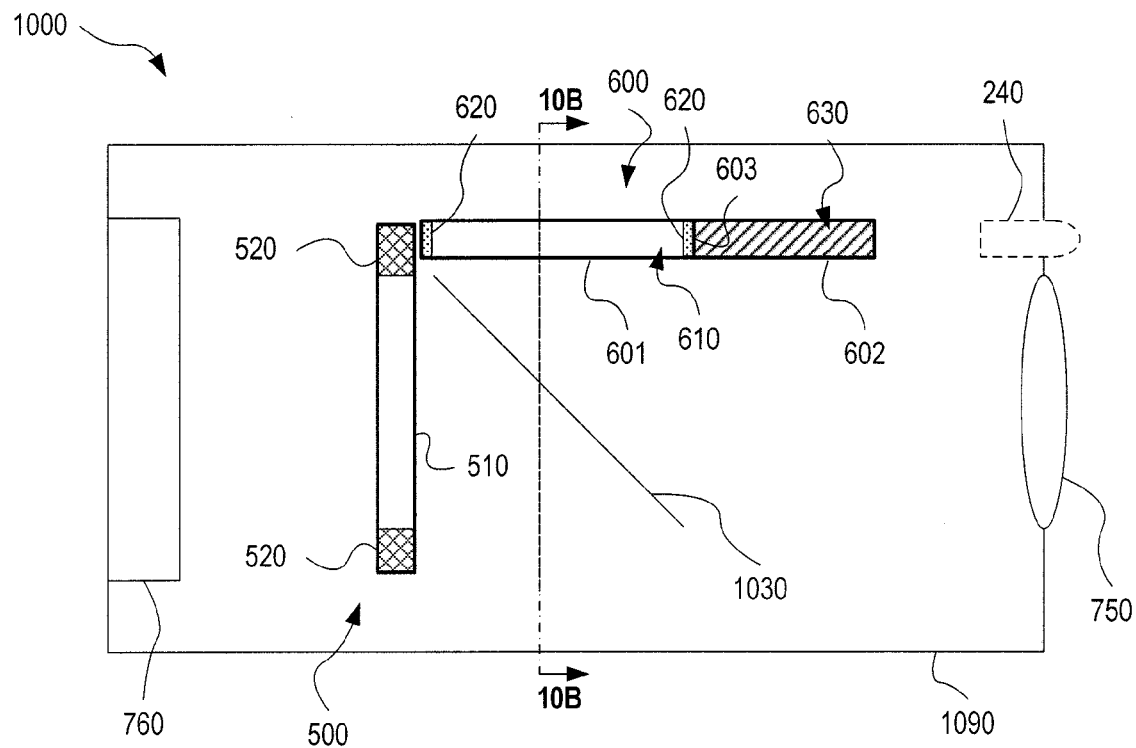
FIG. 10A illustrates, in cross-sectional view, an imaging system for use in a spatially constrained location, and which further includes a second image sensor, according to an embodiment.
Figure 10B:
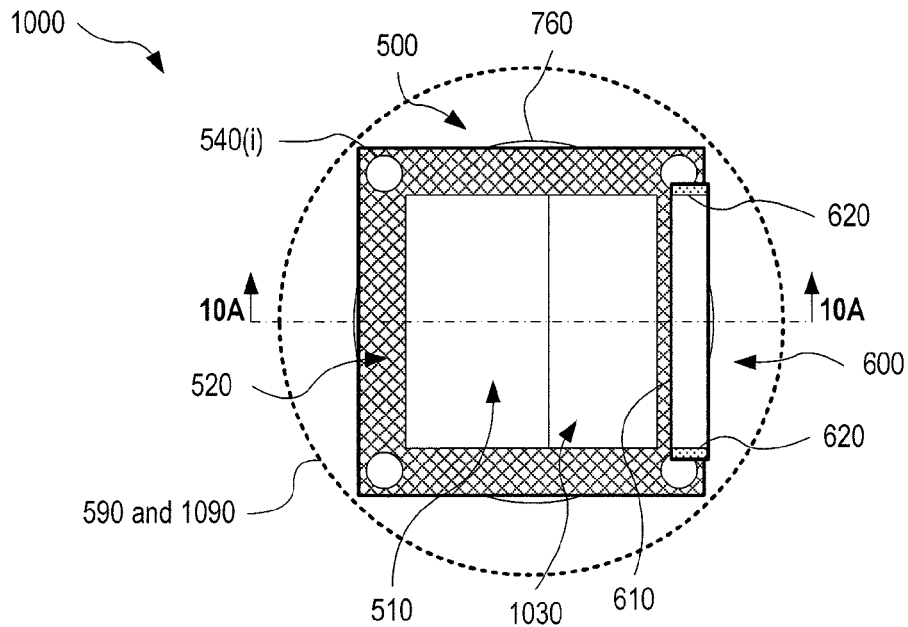
FIG. 10B illustrates the imaging system of FIG. 10A in a cross sectional view orthogonal to the cross sectional view used in of FIG. 10A.

FIGS. 10A and 10B illustrate, in mutually orthogonal cross-sectional views, one exemplary imaging system 1000 for use in a spatially constrained location. FIGS. 10A and 10B are sometimes collectively referred to herein as FIG. 10. Imaging system 1000 is an extension of imaging system 700 of FIG. 7, which further includes a second image sensor. Imaging system 1000 is configured such that its two image sensors may capture images simultaneously. As discussed in connection with FIG. 2, the two image sensors may have different properties. Imaging system 1000 differs from imaging system 700 in three regards: (a) imaging system 1000 further includes prior art image sensor 500 of FIG. 5, (b) reflective surface 1030 replaces reflective surface 730 of imaging system 700, and (c) enclosure 1090 replaces enclosure 790 of imaging system 700. In certain embodiments, imaging system 1000 is implemented in endoscope, such as a medical endoscope.

FIG. 10A shows imaging system 1000 in a cross-sectional view, where the cross section is taken in the plane spanned by the optical axis of imaging objective 750 and a surface normal to pixel array 610. FIG. 10B shows imaging system 1000 in a cross-sectional view, where the cross section is taken in the dimension orthogonal to the optical axis of imaging objective 750 and parallel to a surface normal of pixel array 610, along line 10B-10B in FIG. 10A. Prior art image sensor 500 is located such that the surface normal of pixel array 510 (FIG. 5) is parallel to the optical axis of imaging objective 750. Imaging system 1000 is configured such that prior art image sensor 500 images light transmitted by reflective surface 1030. Reflective surface 1030 is an embodiment of reflective surface 730 with a reflection and transmission coefficients appropriate for directing light towards both image sensor 600 and prior art image sensor 500. Enclosure 1090 is enlarged as compared to enclosure 790 (FIG. 7) in order to accommodate prior art image sensor 500. Accordingly, enclosure 1090 has the same diameter as bounding circle 590 of FIG. 5. This is evident in FIG. 10B, where enclosure 1090 coincides with bounding circle 590.

It is noteworthy that if image sensor 600 and reflective surface 1030 were removed from imaging system 1000, the resulting imaging system would be a conventional imaging system configured, for example, for implementation in a medical endoscope. However, by utilizing the asymmetric configuration of image sensor 600 and the inclusion of reflective surface 1030, imaging system 1000 provides two image sensors within the same enclosure as used for a conventional system. Hence, imaging system 1000 offers improved versatility over the corresponding conventional imaging system.

Imaging system 1000 may be configured with image sensor 905 (FIG. 9) in place of image sensor 600, and, optionally, reflective surface 930 (FIG. 9) in place of reflective surface 1030, without departing from the scope hereof. As evident from FIG. 9, image sensor 900 will fit within enclosure 1090. In this embodiment, imaging system 1000 provides an additional image sensor over the corresponding conventional system, and the additional image sensor has a larger pixel array 910 (FIG. 9) than the pixel array 510 of prior art image sensor 500. This embodiment may provide enhanced imaging capabilities over the conventional system.

Figure 11:
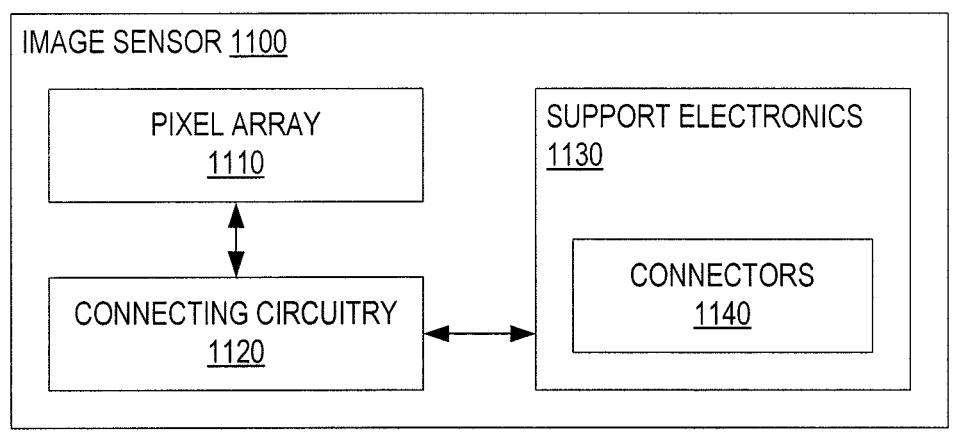
FIG. 11 illustrates an image sensor for use in a spatially constrained location, including a pixel array, support electronics, and connecting circuitry, according to an embodiment.

FIG. 11 illustrates one exemplary image sensor 1100 for imaging in a spatially constrained location. Image sensor 1100 includes a pixel array 1110, connecting circuitry 1120, and support electronics 1130. Support electronics 1130 further includes connectors 1140. Pixel array 1110 is communicatively coupled with connecting circuitry 1120, which in turn is communicatively coupled with support electronics 1130. Pixel array 1110 generates electrical signals in response to light incident thereupon. These electrical signals are communicated to support electronics 1130 via connecting circuitry 1120. Support electronics 1130 generates an electrical image signal from the electrical signals received from pixel array 1110 via connecting circuitry 1120. This electrical image signal is representative of the image formed on pixel array 1110 and may be communicated to an external system using connectors 1140. Support electronics receives electrical signals from outside of image sensor 1100 through connectors 1140. In an embodiment, such electrical signals include power, ground, and a clock signal for operation of image sensor 1100. In another embodiment, the electrical signals received from outside image sensor 1100 further include one or more control signals, such as a gain control signal, an exposure time control signal, a white balance control signal, and a negative voltage necessary for the operation of a pixel array with very small pixels.

In one embodiment, image sensor 1100 is image sensor 600 of FIG. 6. In this embodiment, pixel array 1110 is pixel array 610 (FIG. 6), connecting circuitry 1120 is connecting circuitry 620 (FIG. 6), support electronics 1130 is support electronics 630, and connectors 1140 is connectors 640 (FIG. 6) and, optionally, optional connectors 645 (FIG. 6). In another embodiment, image sensor 1100 is image sensor 905 of FIG. 9. In this embodiment, pixel array 1110 is pixel array 910 (FIG. 9), connecting circuitry 1120 is connecting circuitry 920 (FIG. 9), support electronics 1130 is the support electronics of image sensor 905 (not shown in FIG. 9), and connectors 1140 is the connectors of image sensor 905 (also not shown in FIG. 9). In certain embodiments, image sensor 1100 is implemented in an endoscope, for example a medical endoscope.

Figure 12:
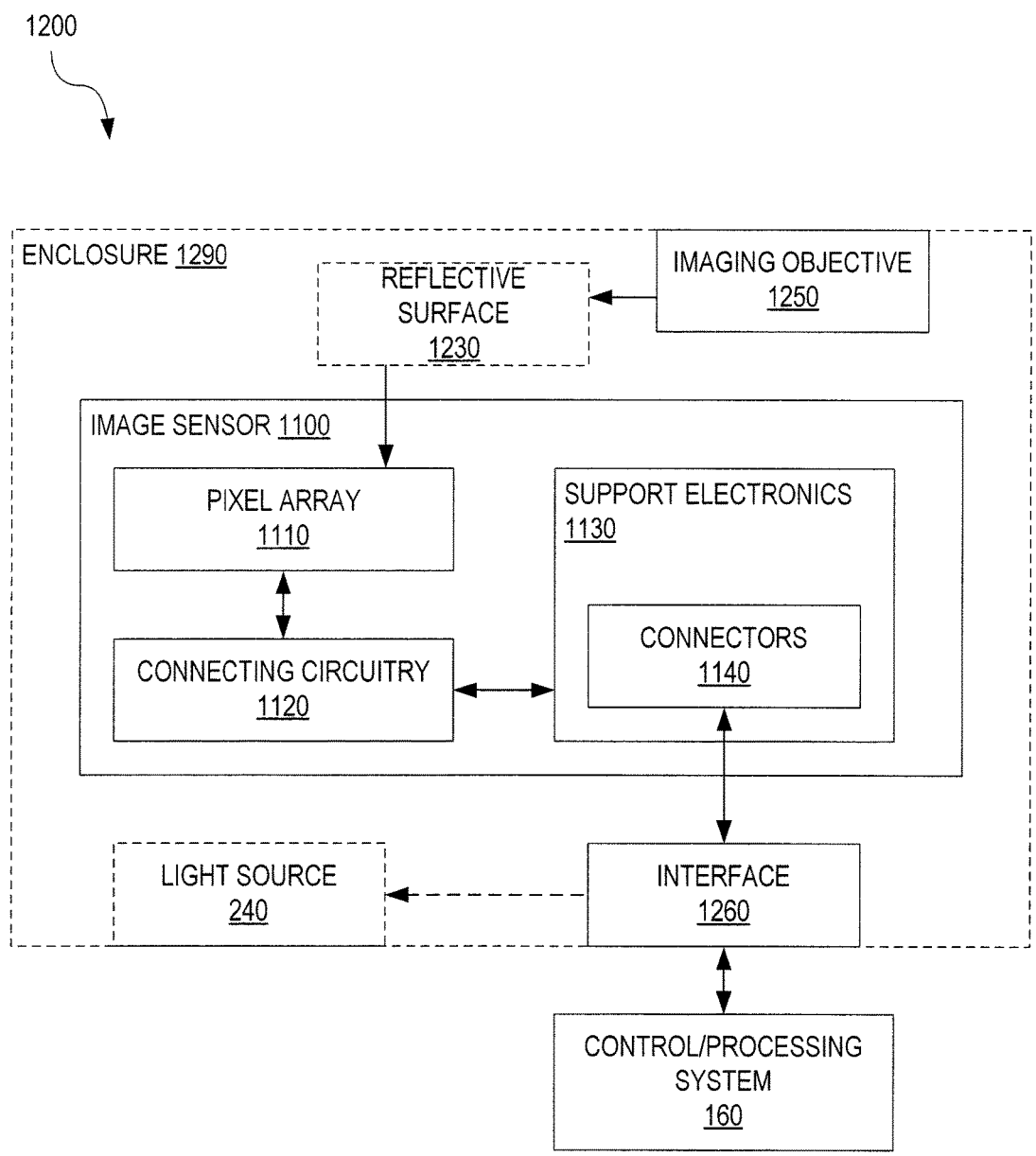
FIG. 12 illustrates an imaging system for use in a spatially constrained location, which utilizes the image sensor of FIG. 11, according to an embodiment.

FIG. 12 illustrates one exemplary imaging system 1200 for use in a spatially constrained location. Imaging system 1200 includes image sensor 1100 of FIG. 11, an imaging objective 1250 for forming an image on pixel array 1110 (FIG. 11), control/processing system 160, and an interface 1260 communicatively coupled with connectors 1140 (FIG. 11) and control/processing system 160 for communicating electrical signals between image sensor 1100 and control/processing system 160 (FIG. 1). In certain embodiments, imaging system 1200 further includes a reflective surface 1230 for redirecting at least a portion of light transmitted by imaging objective 1250 towards pixel array 1100. Imaging system 1200 may further include light source 240 (FIG. 2) communicatively coupled with interface 1260, such that interface 1260 controls light source 240. Alternatively, optional light source 240 is communicatively coupled with connectors 1140 (not shown in FIG. 12) and controlled by support electronics 1130. In an embodiment, imaging system 1200 further includes enclosure 1290 for holding and at least partly enclosing image sensor 1100, imaging objective 1250, interface 1260, optional reflective surface 1230, and optional light source 240. Control/processing system 160 controls image sensor 1290, and optionally light source 240. In addition, control/processing system 160 processes an electrical image signal generated by support electronics 1130. For example, control/processing system 160 generates an image and displays the image to a user, or control/processing system 160 analyzes the electrical image signal.

In one embodiment, image sensor 1100 is image sensor 600 (FIGS. 6 and 7), imaging objective 1250 is imaging objective 750 (FIG. 7), optional enclosure 1290 is enclosure 790 (FIG. 7), interface 1260 is interface 760 (FIG. 7), and optional reflective surface 1230 is reflective surface 730 (FIG. 7), where imaging system 1100 is configured as discussed in connection with FIG. 7. In another embodiment, image sensor 1100 is image sensor 900 (FIG. 9), imaging objective 1250 is imaging objective 750 (FIG. 7), optional enclosure 1290 is enclosure 790 (FIG. 7), interface 1260 is interface 760 (FIG. 7), and optional reflective surface 1230 is reflective surface 730 (FIG. 7), where imaging system 1100 is configured as discussed in connection with FIG. 7. In certain embodiments, imaging system 1200 is implemented in an endoscope, for example a medical endoscope.

Figure 13:
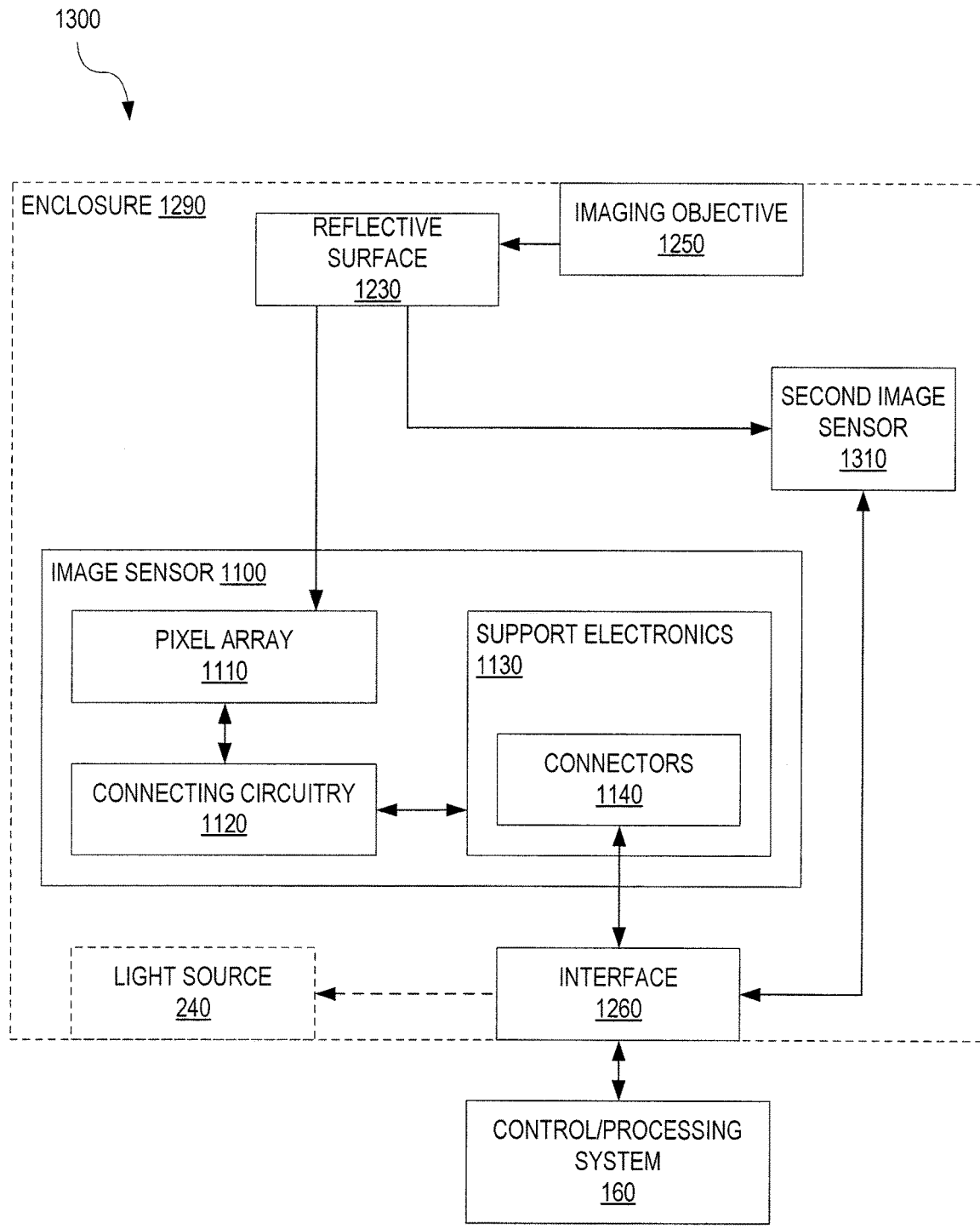
FIG. 13 illustrates an imaging system for use in a spatially constrained location, and which is an extension of the imaging system of FIG. 12 by further including a second image sensor, according to an embodiment.

FIG. 13 illustrates one exemplary imaging system 1300 for use in a spatially constrained location. Imaging system 1300 is an extension of imaging system 1200 (FIG. 12) further including a second image sensor 1310. Image sensor 1100 images at least a portion of light reflected by reflective surface 1230. Second image sensor 1310 is communicatively coupled with reflective surface 1230 and interface 1260. Second image sensor 1310 images at least a portion of light transmitted by reflective surface 1230. In an embodiment, second image sensor 1310 is prior art image sensor 500 (FIG. 5), and imaging system 1300 is configured as discussed in connection with FIG. 10. As discussed in connection with FIGS. 2 and 10, imaging system 1300 provides enhanced versatility and/or performance by providing two image sensors. In certain embodiments, imaging system 1200 is implemented in an endoscope, for example a medical endoscope.

Figure 14:
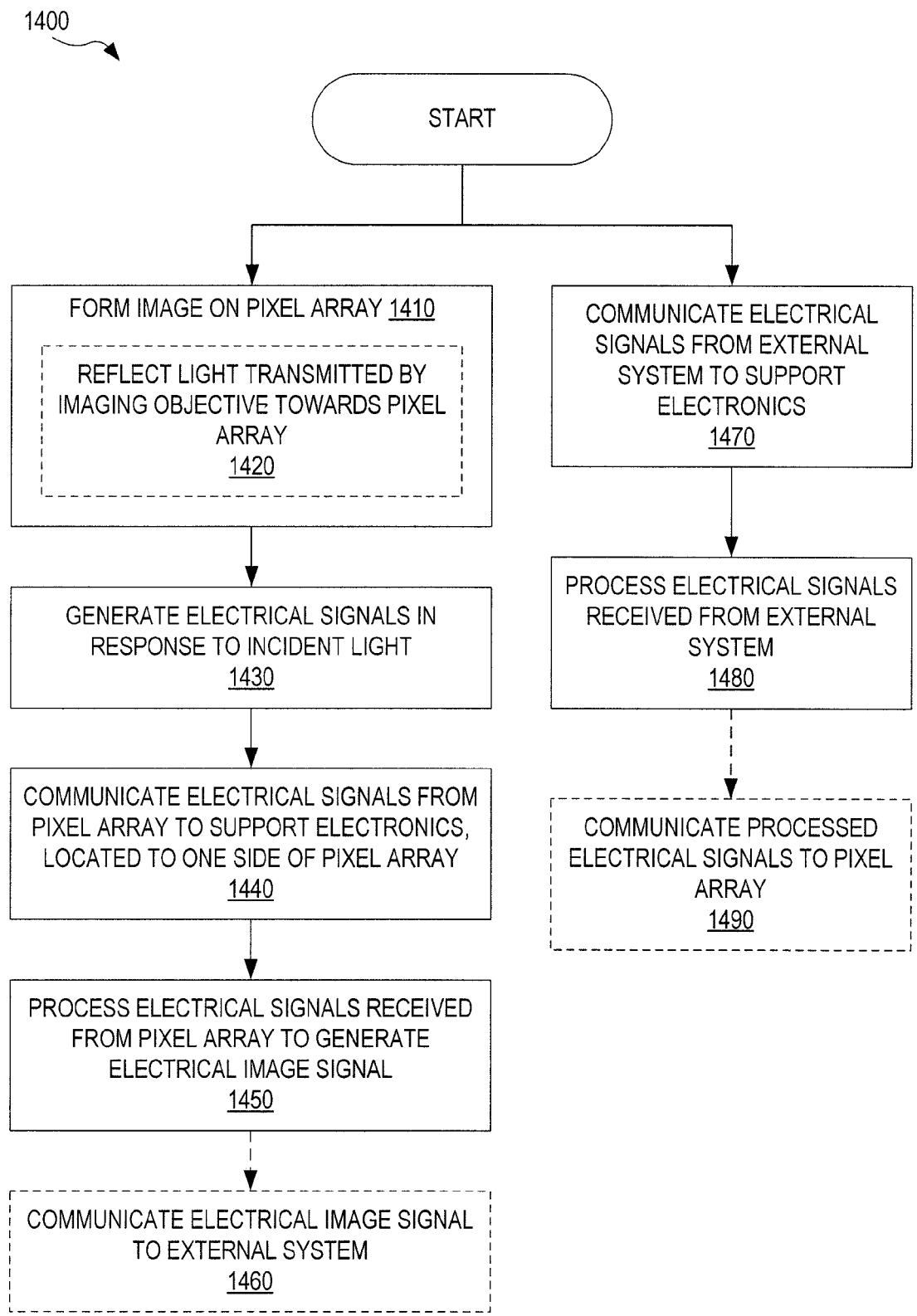
FIG. 14 illustrates an imaging method for use in a spatially constrained location, according to an embodiment.

FIG. 14 illustrates one exemplary imaging method 1400 for use in a spatially constrained location. Imaging method 1400 may be performed by imaging system 700 of FIG. 7. In a step 1410, an imaging objective forms an image of a scene on a pixel array. For example, imaging objective 750 (FIG. 7) forms an image on pixel array 610 of image sensor 600 (FIGS. 6 and 7). Optionally, step 1410 includes a step 1420, wherein at least a portion of light transmitted by the imaging objective is reflected towards the pixel array to form the image. For example, reflective surface 730 (FIG. 7) reflects at least a portion of the light transmitted by imaging objective 750 (FIG. 7) towards pixel array 610 (FIGS. 6 and 7).

In a step 1430, the pixel array generates electrical signals in response to the light incident in step 1410. For example, pixel array 610 (FIGS. 6 and 7) generates electrical signals in response to light incident thereupon from imaging objective 750 (FIG. 7). In a step 1440, electrical signals generated by the pixel array, in response to incident light, are communicated from the pixel array to support electronics located to one side of the pixel array. For example, electrical signals generated by pixel array 610 (FIGS. 6 and 7), in response to incident light, are communicated to support electronics 630 (FIGS. 6 and 7) via connecting circuitry 620 (FIGS. 6 and 7), according to the discussion in connection with FIG. 11. In a step 1450, the support electronics processes the electrical signals received in step 1440 to generate an electrical image signal representative of the image formed on the pixel array in step 1410. For example, support electronics 630 (FIGS. 6 and 7) processes electrical signals received from pixel array 610 (FIGS. 6 and 7) via connecting circuitry 620 (FIGS. 6 and 7) to generate an electrical image signal representative of an image formed on pixel array 610, according to the discussion in connection with FIG. 11. In an optional step 1460, the electrical image signal generated in step 1450 is communicated to an external system. For example, support electronics 630 (FIGS. 6 and 7) uses connectors 640 (FIGS. 6 and 7), and optionally connectors 645 (FIGS. 6 and 7), to communicate an electrical image signal to control/processing system 160 (FIGS. 1 and 12) via interface 760 (FIG. 7), according to the discussion in connection with FIG. 12.

Method 1400 further includes steps 1470 and 1480, and an optional step 1490. These steps are performed in parallel with steps 1410, 1430, 1440, 1450, and, optionally, 1460. In step 1470, an external system communicates electrical signals to the support electronics. Such signals may include, for example, power, ground, a clock signal, and/or control signals for controlling more advanced functionality of the image sensor, such as gain, exposure time, and white balance. For example, control/processing system 160 (FIGS. 1 and 12) communicates power, ground, a clock signal, and a gain control signal to connectors 640 (FIGS. 6 and 7) and/or optional connectors 645 (FIGS. 6 and 7) of support electronics 630 (FIGS. 6 and 7) via interface 760 (FIG. 7), according to the discussion in connection with FIG. 12. In a step 1480, the support electronics processes the electrical signals received in step 1470. For example, support electronics 630 (FIGS. 6 and 7) processes the electrical signals received from control/processing system 160 (FIGS. 1 and 12). In an optional step 1490, one or more electrical signals processed by the support electronics in step 1480 is communicated to the pixel array for proper operation thereof. For example, support electronics 630 (FIGS. 6 and 7) communicates power and ground to pixel array 610 (FIGS. 6 and 7) via connecting circuitry 620 (FIGS. 6 and 7).

Figure 15:
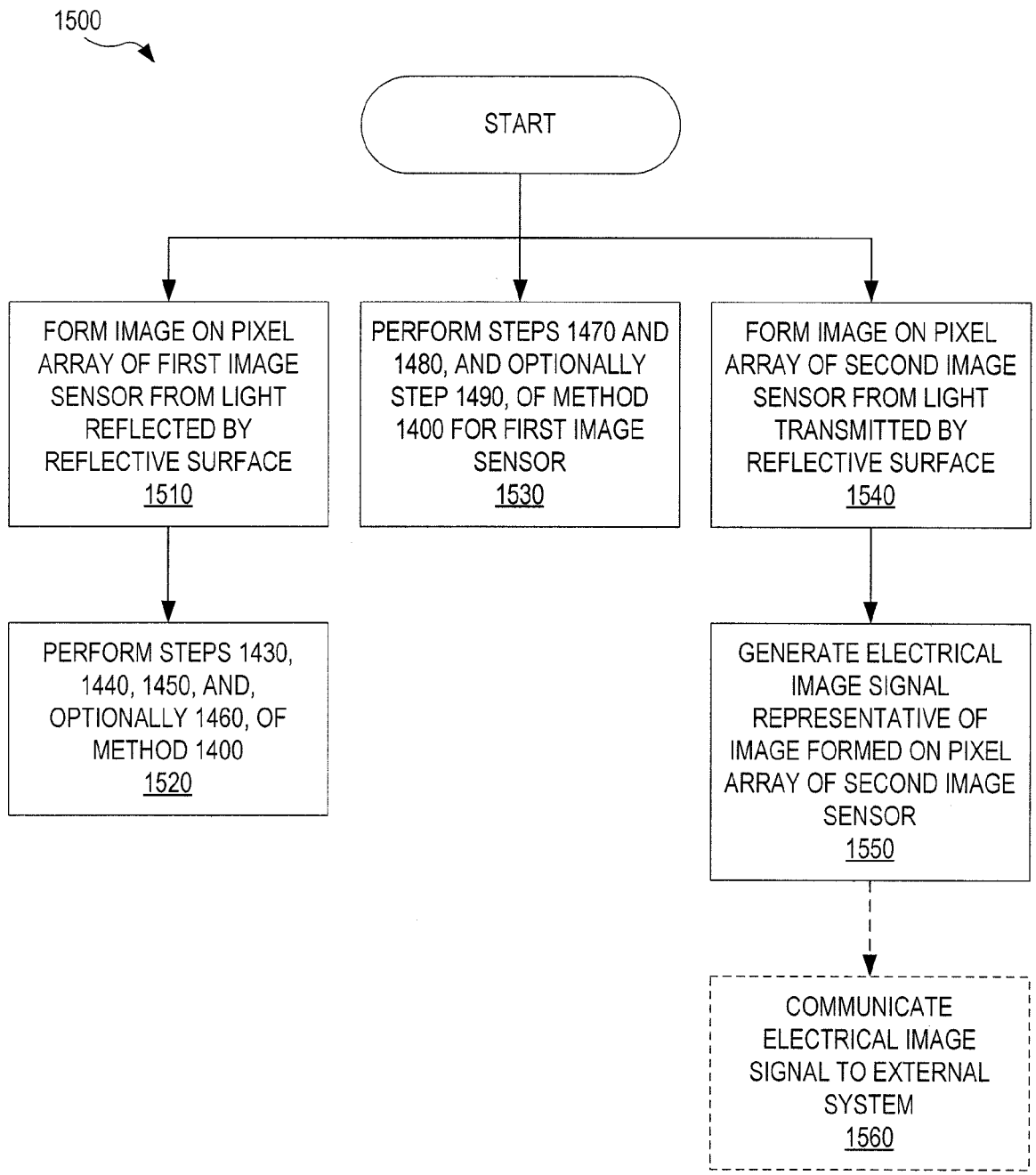
FIG. 15 illustrates an imaging method for use in a spatially constrained location, and which is an extension of the imaging method of FIG. 14 by further including capturing images with a second image sensor, according to an embodiment.

FIG. 15 illustrates one exemplary imaging method 1500 for use in a spatially constrained location. Imaging method 1500 is an extension of imaging method 1400 (FIG. 14) further including obtaining images from a second image sensor. Imaging method 1500 may be performed by system 1000 of FIG. 10. In a step 1510, an imaging objective forms an image of a scene on a pixel array of a first image sensor from at least a portion of light transmitted by the imaging objective and reflected towards the pixel array by a reflective surface. For example, imaging objective 750 (FIG. 7) forms an image on pixel array 610 of image sensor 600 (FIGS. 6 and 7), with reflective surface 730 (FIG. 7) reflecting at least a portion of the light transmitted by imaging objective 750 (FIG. 7) towards pixel array 610 (FIGS. 6 and 7). In a step 1520, imaging method 1500 performs steps 1430, 1440, 1450, and, optionally 1460, of method 1400 for the first image sensor as discussed in connection with FIG. 14. In a step 1530, performed in parallel with steps 1510 and 1520, imaging method 1500 performs steps 1470 and 1480, and optionally step 1490, of method 1400 for the first image sensor as discussed in connection with FIG. 14.

In parallel with performing steps 1510, 1520, and 1530, imaging method 1500 performs steps 1540 and 1550, and optionally step 1560. In step 1540, an image is formed on the pixel array of a second image sensor from at least a portion of light transmitted by the objective and the reflective surface, where the objective and the reflective surface are the same as used in step 1510. For example, an image is formed on pixel array 510 (FIGS. 5 and 10) of prior art image sensor 500 (FIGS. 5 and 10) from at least a portion of light transmitted by imaging objective 750 (FIGS. 7 and 10) and reflective surface 1030 (FIG. 10). In a step 1550, the second image sensor generates an electrical image signal representative of the image formed on the pixel array of the second image sensor in step 1540. For example, prior art image sensor 500 (FIGS. 5 and 10) generates an electrical image signal representative of the image formed on pixel array 510 (FIGS. 5 and 10) using methods known in the art. Necessary electrical signals are communicated thereto from an external system, for example control/processing system 160 (FIGS. 1 and 12), through interface 760. In an optional step 1560, the electrical image signal generated by the second image sensor is communicated to an external system. For example, prior art image sensor 500 (FIGS. 5 and 10) communicates the electrical image signal to an external system, such as control/processing system 160 (FIGS. 1 and 12) via interface 760.

Combinations of Features

Features described above as well as those claimed below may be combined in various ways without departing from the scope hereof. For example, it will be appreciated that aspects of one imaging system or method for use in a spatially constrained location described herein may incorporate or swap features of another imaging system or method for use in a spatially constrained location described herein. The following examples illustrate possible, non-limiting combinations of embodiments described above. It should be clear that many other changes and modifications may be made to the methods and system herein without departing from the spirit and scope of this invention:

(A) An imaging system for use in a spatially constrained location may include a first image sensor for capturing an image and having (a) a first rectangular area containing a pixel array and connecting circuitry communicatively coupled with the pixel array and (b) a second rectangular area with only one shared side with the first rectangular area and containing support electronics for pixel array control and signal acquisition, where the support electronics is communicatively coupled with the connecting circuitry.

(B) In the imaging system denoted as (A), the shared side may have a length defined by extent of the pixel array and the connecting circuitry in a dimension parallel to the shared side.

(C) In the imaging systems denoted as (A) and (B), the pixel array may be rectangular with a longer side and a shorter side, where the longer side and shorter side are mutually orthogonal and the shorter side is parallel to the shared side.

(D) In the imaging systems denoted as (A) through (C), the support electronics may include at least six connectors for forming electrical contacts with a system external to the first image sensor.

(E) In the imaging system denoted as (D), the support electronics may be configured for receiving signals from the electrical contacts for controlling at least one of exposure time, gain, and white balance.

(F) The imaging systems denoted as (A) through (E) may further include an imaging objective for forming the image and having a first optical axis oriented at an non-zero angle to a surface normal of the pixel array.

(G) The imaging system denoted as (F) may further include a reflective surface for reflecting at least a portion of light, transmitted by the imaging objective, towards the pixel array.

(H) In the imaging system denoted as (G), the optical axis may be substantially orthogonal to the surface normal.

(I) In the imaging system denoted as (H), the shared side may be substantially orthogonal to the optical axis and the surface normal.

(J) In the imaging systems denoted as (G) through (I), the reflective surface may be configured to reflect the at least a portion of light by internal reflection.

(K) In the imaging systems denoted as (G) through (I), the reflective surface may be a surface of a mirror.

(L) In the imaging systems denoted as (G) through (J), the reflective surface may be an interface between two elements.

(M) In the imaging systems denoted as (A) through (L), the first image sensor may be a CMOS image sensor.

(N) In the imaging systems denoted as (A) through (L), the first image sensor may be a CCD image sensor.

(O) The imaging systems denoted as (A) through (M) may further include an enclosure.

(P) The imaging systems denoted as (G) through (M) may further include an enclosure for holding the first image sensor, the reflective surface, and the imaging objective such that the system has an extent of no more than 10 millimeters in dimensions orthogonal to the first optical axis.

(Q) The imaging systems denoted as (A) through (P) may further include a system external to the first image sensor for control of functionality of the first image sensor and/or processing of images captured by the first image sensor.

(R) The imaging systems denoted as (G) through (Q) may further include a second image sensor for capturing an image formed from at least a portion of light from the imaging objective and the reflective surface.

(S) In the imaging system denoted as (R), the at least a portion of light from the imaging objective and the reflective surface may be transmitted by the reflective surface.

(T) In the imaging systems denoted as (R) and (S), the second image sensor may have at least one property that is different from a corresponding property of the first image sensor.

(U) In the imaging systems denoted as (R) through (T), the second image sensor may be a CMOS image sensor.

(V) In the imaging systems denoted as (R) through (T), the second image sensor may be a CCD image sensor.

(W) The imaging systems denoted as (R) through (V) may further include a system external to the first and second image sensors for control of functionality of at least one of the first and second image sensors and/or processing of images captured by at least one of the first and second image sensors.

(X) The imaging systems denoted as (A) through (R) may be implemented in a medical endoscope.

(Y) An imaging method for use in a spatially constrained location may include (i) forming an image of a scene on a pixel array of an image sensor contained within a first rectangular area having a first side and (ii) communicating first electrical signals between the pixel array and support electronics located onboard the image sensor and contained within a second rectangular area sharing only one side with the first rectangular area.

(Z) The imaging method denoted as (Y) may further include processing first electrical signals received from the pixel array, using the support electronics, to generate an electrical image signal representative of the image.

(AA) The imaging method denoted as (Z) may further include communicating the electrical image signal from the support electronics to a control/processing system external to the image sensor.

(AB) The imaging methods denoted as (Y) and (Z) may further include communicating electrical control signals from a control/processing system to the image sensor.

(AC) The imaging method denoted as (AA) may further include communicating electrical control signals from a control/processing system to the image sensor.

(AD) In the imaging methods denoted as (AB) and (AC), the step of communicating electrical control signals may include communicating electrical control signals for controlling at least one of exposure time, gain, and white balance.

(AE) In the imaging methods denoted as (Y) through (AD), the step of forming an image may further include utilizing an imaging objective.

(AF) In the imaging method denoted as (AE), the step of forming an image may further include reflecting at least a portion of light transmitted by the imaging objective to direct the at least a portion of light towards the image sensor, where the imaging objective has an optical axis substantially orthogonal to a surface normal of the image sensor.

(AG) The imaging methods denoted as (AA) through (AF) may further include forming an image on a second image sensor.

(AH) The imaging method denoted as (AE) may further include forming an image on a second image sensor from at least a portion of light transmitted by the imaging objective and transmitted by the reflective surface.

Changes may be made in the above systems, devices, and methods without departing from the scope hereof. It should thus be noted that the matter contained in the above description and shown in the accompanying drawings should be interpreted as illustrative and not in a limiting sense. The following claims are intended to cover generic and specific features described herein, as well as all statements of the scope of the present systems, devices, and methods, which, as a matter of language, might be said to fall therebetween.

What is claimed is:

1. Imaging system for use in a medical endoscope, comprising:
a first image sensor for capturing a medical endoscope image and including (a) a first rectangular area containing a pixel array and connecting circuitry communicatively coupled with the pixel array and (b) a second rectangular area having only one shared side with the first rectangular area and containing support electronics for pixel array control and signal acquisition, the support electronics being communicatively coupled with the connecting circuitry;
an imaging objective for forming the medical endoscope image and having a first optical axis oriented at an non-zero angle to a surface normal of the pixel array; and
a reflective surface configured to spectrally non-selectively reflect toward the pixel array at least a first portion of light transmitted by the imaging objective;
wherein the first image sensor, the imaging objective, and the reflective surface are cooperatively configured for implementation of the imaging system in the medical endoscope.

2. Imaging system of claim 1, the shared side having a length defined by extent of the pixel array and the connecting circuitry in a dimension parallel to the shared side.

3. Imaging system of claim 1, the pixel array being rectangular with a longer side and a shorter side, the longer side and shorter side being mutually orthogonal and the shorter side being parallel to the shared side.

4. Imaging system of claim 1, the support electronics comprising at least six connectors for forming electrical contacts with a system external to the first image sensor.

5. Imaging system of claim 4, further comprising the system external to the first image sensor.

6. Imaging system of claim 4, the support electronics being configured for receiving signals from the electrical contacts for controlling at least one of exposure time, gain, and white balance.

7. Imaging system of claim 1, the optical axis being substantially orthogonal to the surface normal.

8. Imaging system of claim 1, the shared side being substantially orthogonal to the optical axis and the surface normal.

9. Imaging system of claim 1, the reflective surface configured to reflect the at least a portion of light by total internal reflection.

10. Imaging system of claim 1, the reflective surface being a surface of a mirror.

11. Imaging system of claim 1, the reflective surface being a contact interface between two elements.

12. Imaging system of claim 1, further comprising a medical endoscope enclosure for holding the first image sensor, the reflective surface, and the imaging objective, the imaging system having an extent of no more than 10 millimeters in dimensions orthogonal to the first optical axis.

13. Imaging system of claim 1, being implemented in the medical endoscope.

14. Imaging system of claim 1, further comprising a second image sensor for capturing an image formed from at least a portion of light from the imaging objective transmitted by the reflective surface.

15. Imaging system of claim 14, the second image sensor having at least one property that is different from a corresponding property of the first image sensor.

16. An imaging method for use in a medical endoscope, comprising:
    forming, using an imaging objective having an optical axis and positioned at least partly within a medical endoscope enclosure, a first medical endoscope image of a scene on a pixel array of an image sensor having surface normal oriented at a non-zero angle to the optical axis and positioned within the medical endoscope enclosure, the pixel array being contained within a first rectangular area having a first side, said forming including reflecting, without spectrally selecting, at least a first portion of light transmitted from the scene by the imaging objective to direct the first portion to the pixel array; and
    communicating first electrical signals between the pixel array and support electronics located onboard the image sensor and contained within a second rectangular area sharing only one side with the first rectangular area.

17. The imaging method of claim 16, further comprising processing first electrical signals received from the pixel array, using the support electronics, to generate an electrical image signal representative of the first medical endoscope image.

18. The imaging method of claim 16, further comprising communicating the electrical image signal from the support electronics to a control/processing system external to the image sensor.

19. The imaging method of claim 18, further comprising communicating electrical control signals from the control/processing system to the image sensor.

20. The imaging method of claim 19, the step of communicating electrical control signals comprising communicating electrical control signals for controlling at least one of exposure time, gain, and white balance.

21. The imaging method of claim 16, in the step of forming, the optical axis being substantially orthogonal to the surface normal.

22. The imaging method of claim 16, the step of reflecting comprising:
    reflecting the first portion on a reflective surface; and
    forming a second medical endoscope image on a second image sensor, positioned within the medical endoscope enclosure, from a second portion of light transmitted by the imaging objective and transmitted by the reflective surface.

23. The imaging method of claim 22, the reflective surface being spectrally non-selective, the step of reflecting comprising forming the first medical endoscope image and the second medical endoscope image from light of same spectral content.

* * * * *